(12) United States Patent
Plessala et al.

(10) Patent No.: US 11,849,972 B2
(45) Date of Patent: Dec. 26, 2023

(54) DEVICE AND METHOD FOR IMPROVING IMPLANTATION OF FERTILIZED EGG DURING PREGNANCY

(71) Applicant: InnoMed Five, LLC, Mobile, AL (US)

(72) Inventors: Kirby J. Plessala, Mobile, AL (US); Peter T. Falkner, Mobile, AL (US); Michael Haddad, Atlanta, GA (US)

(73) Assignee: InnoMed Five, LLC, Mobile, AL (US)

( * ) Notice: Subject to any disclaimer, the term of this patent is extended or adjusted under 35 U.S.C. 154(b) by 94 days.

(21) Appl. No.: 17/409,903

(22) Filed: Aug. 24, 2021

(65) Prior Publication Data

US 2021/0378709 A1 Dec. 9, 2021

Related U.S. Application Data

(63) Continuation of application No. 16/793,624, filed on Feb. 18, 2020, now abandoned, which is a continuation of application No. PCT/US2019/028630, filed on Apr. 23, 2019.

(60) Provisional application No. 62/814,910, filed on Mar. 7, 2019, provisional application No. 62/662,253, filed on Apr. 25, 2018.

(51) Int. Cl.
*A61B 17/00* (2006.01)
*A61B 17/435* (2006.01)
*A61B 17/42* (2006.01)

(52) U.S. Cl.
CPC ...... *A61B 17/435* (2013.01); *A61B 17/00234* (2013.01); *A61B 2017/0046* (2013.01); *A61B 2017/00238* (2013.01); *A61B 2017/4216* (2013.01)

(58) Field of Classification Search
CPC ............ A61B 17/435; A61B 17/00234; A61B 2017/00238; A61B 2017/0046; A61B 2017/4216
See application file for complete search history.

(56) References Cited

U.S. PATENT DOCUMENTS

| | | | | |
|---|---|---|---|---|
| 3,796,211 A * | 3/1974 | Kohl | ................ | A61B 10/0291 606/205 |
| 5,476,104 A * | 12/1995 | Sheahon | ............ | A61B 10/0291 600/570 |
| 5,807,239 A * | 9/1998 | DiBernardo | ............. | A61B 1/07 600/114 |
| 6,610,005 B1 * | 8/2003 | Tao | .................... | A61M 25/0111 604/3 |
| 2002/0010457 A1 * | 1/2002 | Duchon | ................ | A61F 2/0063 600/407 |

* cited by examiner

*Primary Examiner* — Kaylee R Wilson
(74) *Attorney, Agent, or Firm* — Intellectual Property Consulting, LLC; Stephen M. Kepper

(57) ABSTRACT

The disclosed invention comprises a device that utilizes a manually controlled articulating arm to make a precise, small abrasion on the intrauterine wall prior to ovulation. The preferred embodiment of the invention comprises a handle, an arm having a rigid portion and an articulating tip both of which are covered by a casing having non-irritant properties, wherein the handle is connected to the arm by a connection member that contains a trigger mechanism operable to move the articulating tip by pulling a trigger.

3 Claims, 6 Drawing Sheets

DEVICE AND METHOD FOR IMPROVING IMPLANTATION OF FERTILIZED EGG DURING PREGNANCY

RELATED APPLICATIONS

This application is a continuation of U.S. patent application Ser. No. 16/793,624, filed Feb. 18, 2020, and International Application No. PCT/US2019/028630, filed Apr. 23, 2019, which claims the benefit of U.S. Provisional Patent Application No. 62/814,910, filed Mar. 7, 2019 and U.S. Provisional Application No. 62/662,253, filed Apr. 25, 2018. The entire contents of the above applications are hereby incorporated by reference as though fully set forth herein.

FIELD

The present invention relates in general to medical devices. More specifically, the present invention relates to a device and method for improving the intrauterine environment prior to and during pregnancy.

BACKGROUND

Artificial reproductive technology ("ART") is not a new concept. There exists a plethora of issues that may prevent or decrease the likelihood of a successful pregnancy. Although ART has made specific technological advances in order to solve the recurring problems with female fertility, very little has been done to increase the chances of a fertilized egg successfully implanting itself onto the lining of the uterus—a critical step during the pregnancy process.

Once the egg is fertilized, it must then successfully implant itself on the wall of the uterus so that placentation can occur, which allows the fertilized egg to receive necessary nutrients from the mother. Unfortunately, although fertilization may be successful, repeated implantation failure ("RIF") often occurs in mothers using ART; such failures are often attributed to abnormalities in the endometrium at the time of implantation or the mother's immune system.

Currently, physicians will intentionally scratch the endometrium layer of the uterus in order to trigger an inflammatory response within the uterine cavity prior to ovulation. The body's natural wound healing response following the scratch improves the environment of the endometrium and makes it more likely for an embryo to implant and create a pregnancy.

As of now, there is no device tailored to creating a precision "scratch" along the endometrium layer of the uterus. Presently, medical professionals will take a catheter, or some other similar device, and blindly push the catheter forward until they feel some form of resistance; believing the resistance is caused by the uterine wall, the medical professional will start scratching. This seemingly archaic and barbaric way of performing the procedure leads to unnecessary deep punctures, or even a complete perforation in the uterine wall.

Accordingly, there is a strong need for a device that can be manually controlled and guided into the uterus with precision so as to avoid unnecessary trauma and injury.

BRIEF SUMMARY OF THE INVENTION

The subject invention solves this problem by allowing the physician to carefully guide the device through the cervix and into the uterine cavity. Additionally, once in the uterus, the device's articulating arm allows the medical professional to make a precise, small abrasion on the endometrium wall while avoiding the risk of puncturing or penetrating the uterine wall.

The preferred embodiment of the invention is shown in the figures and comprises a handle, an arm having a rigid portion and an articulating tip both of which are covered by a casing, wherein the handle is connected to the arm by a connection member that contains a spring-loaded trigger mechanism operable to move the articulating tip by pulling a trigger. Preferably, the degree of articulation is directly proportionate with the degree that trigger is pulled towards the handle. The proximal end of the arm may further comprise a rotatable knob that is operable to adjust the planar direction of the articulating tip. It is another aspect of this invention that the exterior surface of the arm contain measurement markings that operate to inform the physician of the length of the arm that has been inserted into the patient.

BRIEF DESCRIPTION OF THE DRAWINGS

FIG. 1 is a perspective view of the device showing the trigger mechanism contained within the connecting member.

FIG. 2 is a profile view of the device showing the opposite side from that depicted in FIG. 1.

FIG. 3 is an exploded view of the device.

FIG. 4 is a topside view of the arm.

FIG. 5 is a transparent perspective view of the connecting member showing the trigger mechanism.

FIG. 6 is a perspective view of the device showing the articulating tip in a curled position.

DETAILED DESCRIPTION

Figure 1:
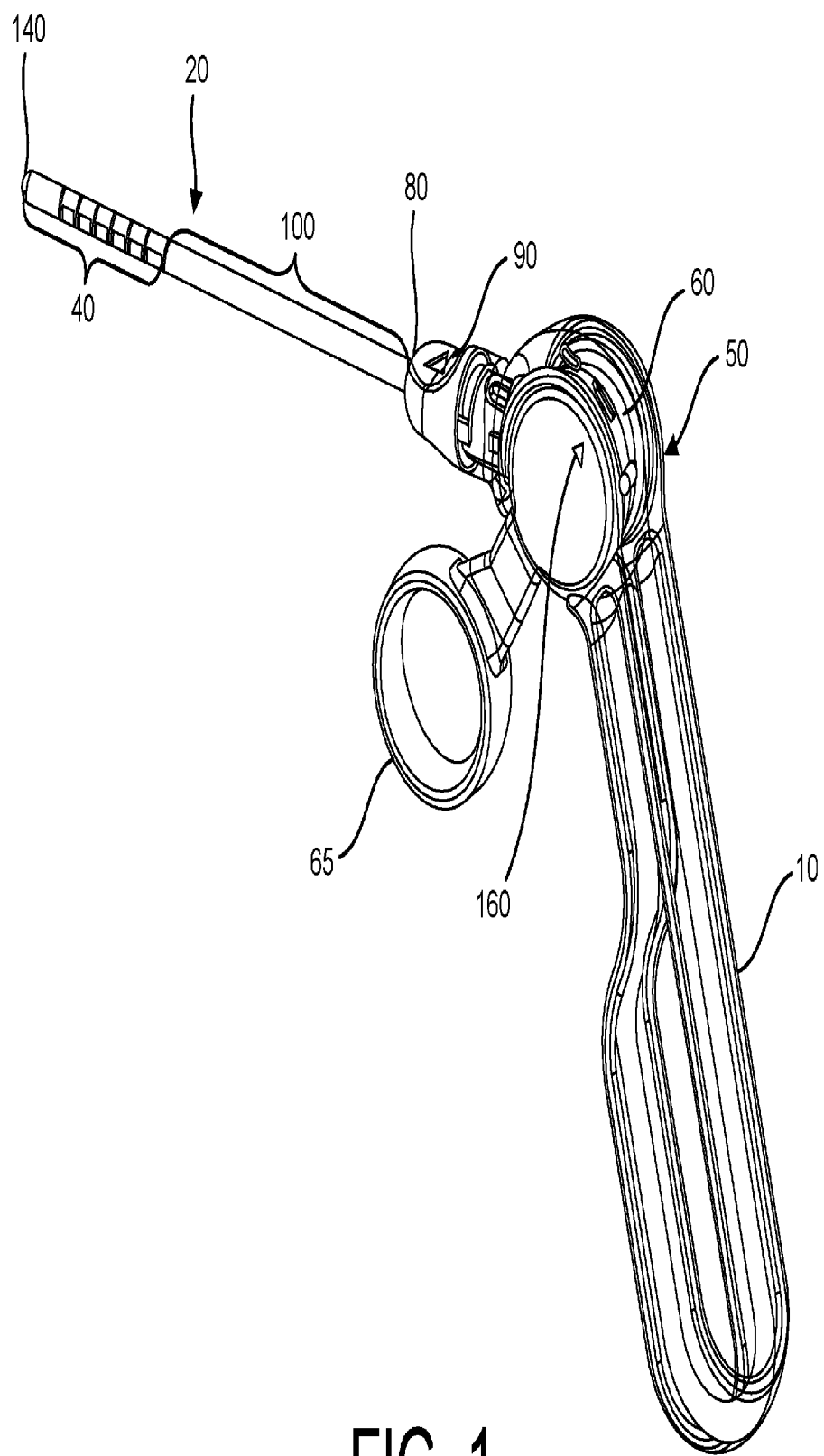
FIG. 1.
Figure 2:
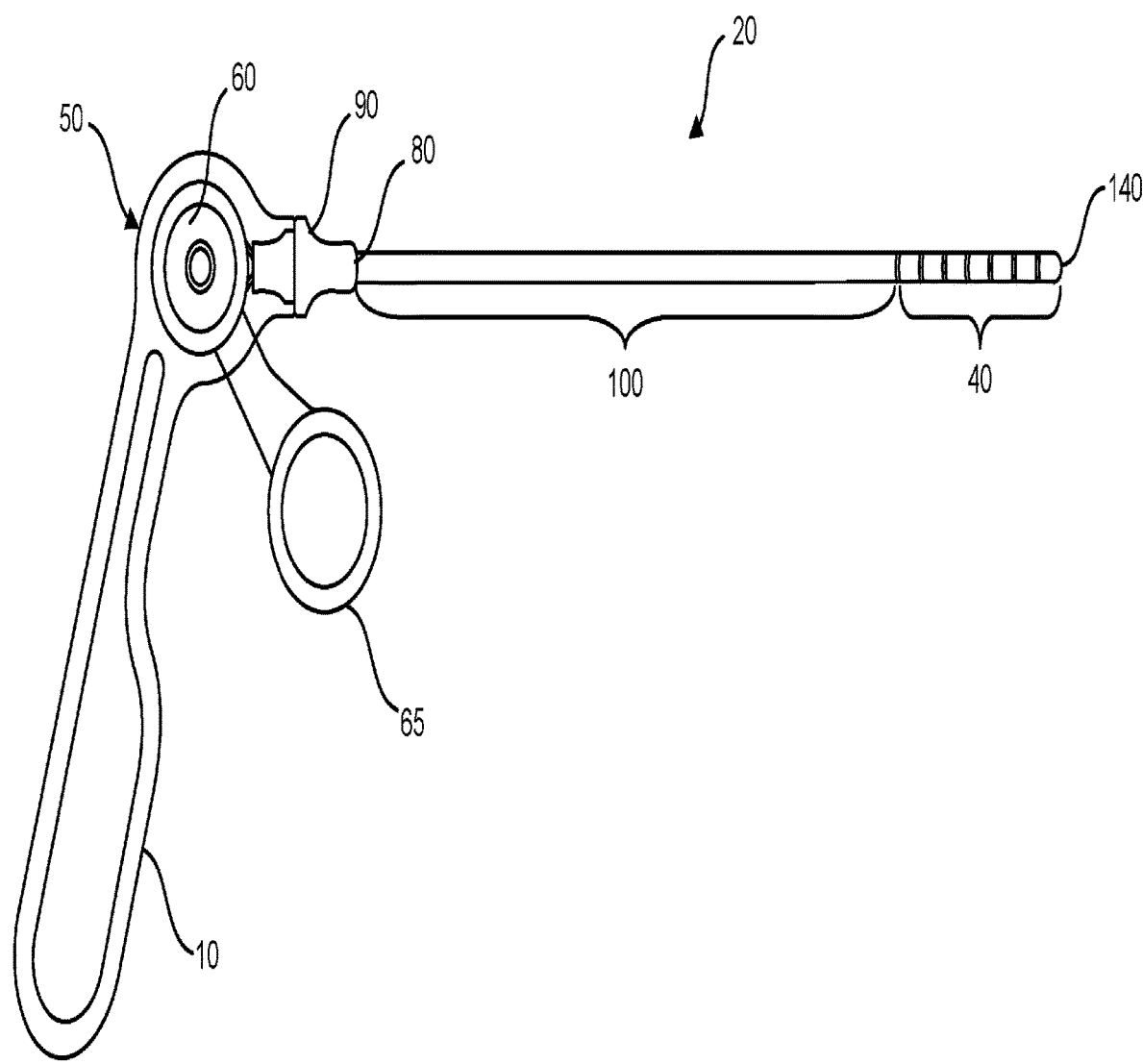
FIG. 2.
Figure 3:
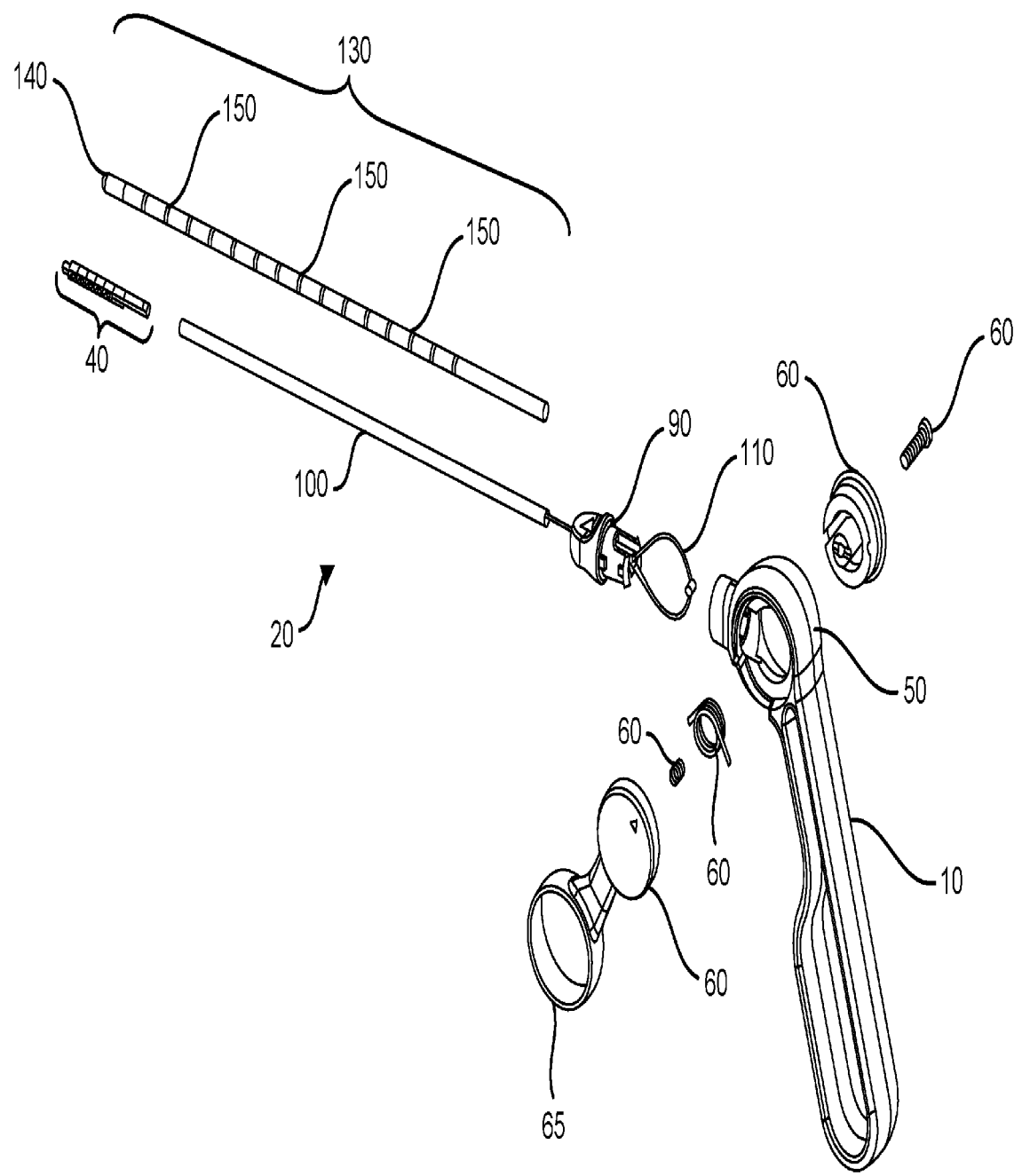
FIG. 3.

Turning to FIGS. 1-3, the preferred embodiment of the subject invention comprises a handle 10, an arm 20 comprising an articulating tip 40, wherein the handle 10 is connected to the arm 20 by a connection member 50 that contains a spring-loaded trigger mechanism 60 operable to curl the articulating tip 40 in a variety of planar directions by pulling a trigger 65. Preferably, the handle 10 is offset approximately 45° from the longitudinal plane of the arm 20 to allow for easier guidance of the arm 20 into the uterine cavity, and said handle 10 is positioned such that the index finger (not shown) of the user can easily actuate the trigger 65.

Figure 4:
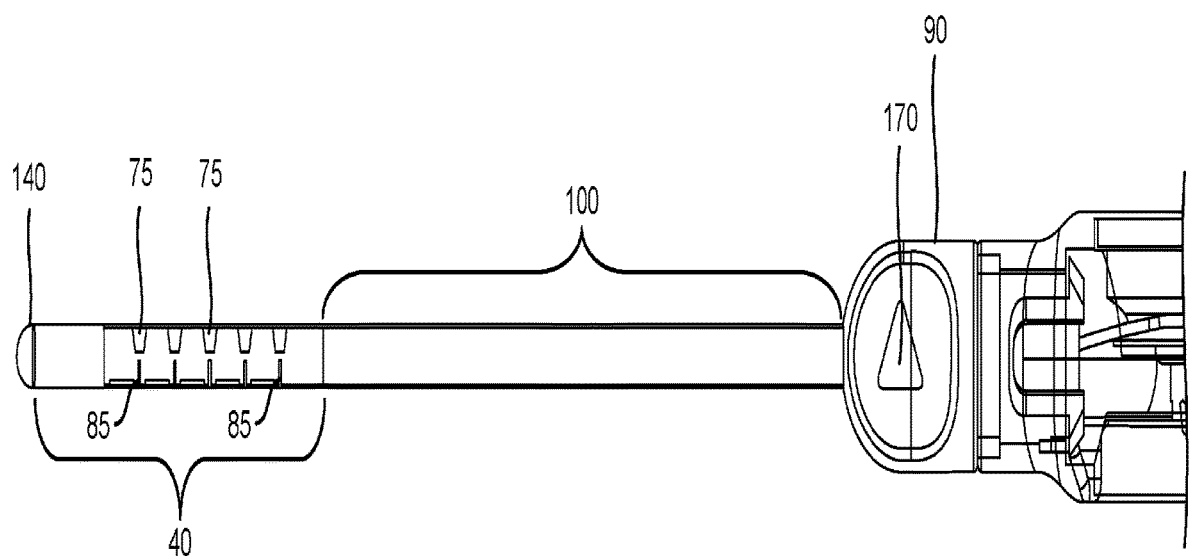
FIG. 4.
Figure 6:
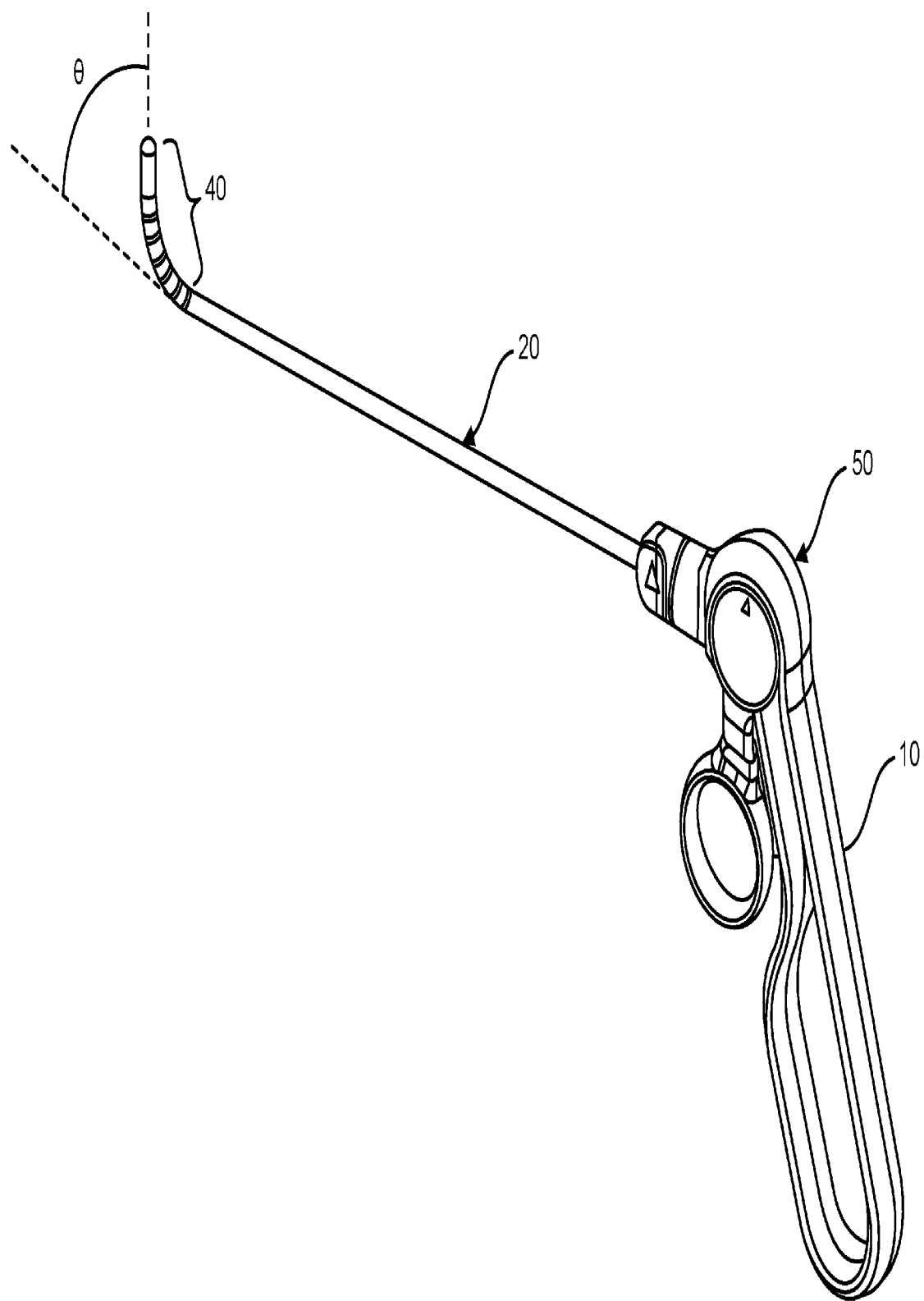
FIG. 6.

Turning to FIG. 4, the articulating tip 40 at the distal end of the arm 20 is made from a material having flexible properties, including but not limited to, flexible polymers, solid foam, thermoplastics, thermoset materials, or other materials known in the art with similar properties. When activated the articulating tip 40 will curl in a given planar direction wherein the inner portion of the curled tip 40 will be compressed and the outer portion of the curled tip 40 will be in tension (as shown in FIG. 6). Accordingly, it is preferable that the articulating tip 40 shall have larger circumferential slits 75 on the inner portion of the tip 40 and smaller circumferential slits 85 on the outer portion of the tip 40 to allow the articulating tip 40 to curl.

The proximal end of the arm comprises a rotatable knob 90 that is operable to adjust the planar direction of the articulating tip 40. The non-flexible portion 100, or rigid portion of the arm 20 positioned between the rotatable knob 90 and the articulating tip 40, is made from a substantially rigid material, e.g. metals or hardened polymers (e.g. carbon fiber or other plastics), to prevent flexion along that portion 100 of the arm 20. For the preferred embodiment, the rotatable knob 90 comprises an indicator, e.g. an arrow 170, which alerts the user as to the planar direction the articulating tip 40 shall curl.

Figure 5:
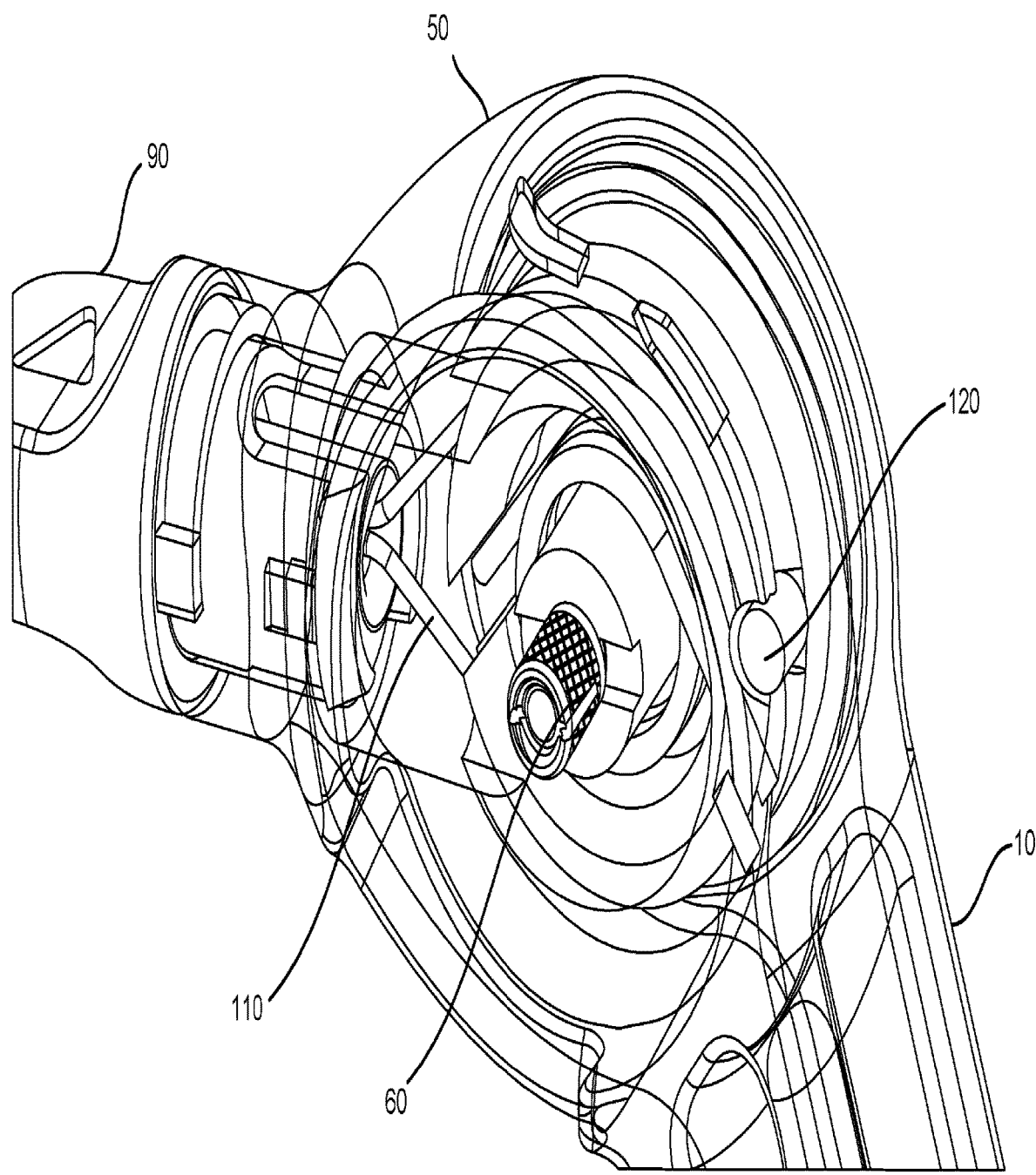
FIG. 5.

As shown in the figures, a cable or wire 110 extends longitudinally from the distal end of the arm 20 and wraps around the spring-loaded trigger mechanism 60 before returning to the distal end of the arm 20 such that a continuous closed loop is formed; a portion of the cable 110 is fixedly attached to the trigger mechanism 60 by a slot-pin 120 (as shown in detail in FIG. 5) or some other attachment means known in the art. Alternatively, the invention anticipates using at least two separate cables or wires 110 that follow a similar path and are in parallel, where one end of the wire is fixedly attached to the trigger mechanism 60 and the opposite end of each wire 110 is fixedly attached at the distal end of the arm 20. For either arrangement, when the trigger 65 is actuated, the trigger mechanism 60 causes one portion of the cable 110 in the arm 20 to slack while the other portion is pulled in tension. This process enables the flexible articulating tip 40 to curl in the direction that the cable 110 is being pulled, thus creating the annular curve θ (as shown in FIG. 6). The degree of annular curve θ created by the articulating tip 40 is directly proportionate to the degree that trigger 65 is pulled towards the handle 10. As shown in the figures, the exterior surface of the trigger mechanism 60 has an arrow 160, which will rotate in an opposite direction of the handle 10 when pulled. As a means to alert the user as to the degree of annular curve θ, the arrow 160 will correspond to measurement markings on the exterior housing (not shown) of the connecting member 50.

Turning to FIGS. 3 and 4, the preferred embodiment further comprises a sleeve 130 that is adapted to fit over and fully enclose the arm 20; a cap portion 140 of the sleeve 130 covers the distal end of the articulating tip 40. The sleeve may be made from any fabric, polymer, or other material that is flexible and has properties that will either minimize or not cause irritation to the patient. As shown in FIG. 4, the preferred embodiment of the cap portion 140 comprises a rounded surface to further minimize irritation to the patient when in contact with the endometrium layer of the uterus. Although this embodiment is preferred, it is envisioned that the cap portion 140 may come in different sizes, shapes, and materials depending on the needs of the user.

As shown in FIG. 3, it is another aspect of this invention that the exterior surface of the sleeve 130 contain measurement markings 150 that operate to inform the physician of the length of the arm 20 that has been inserted into the patient. Although not required, it is preferred that these markings be spaced apart in one-centimeter increments.

The subject device is to be deployed inside the uterus in order to perform a small, precise abrasion along the endometrium layer of the uterus. For optimal results, the procedure will take place in the days leading up to ovulation; often, this occurs on day 7, 8, or 9 of a menstrual cycle, depending on the patient. Using the handle 10, the physician shall guide the arm 20 through the cervix and into the uterine cavity of the patient until the cap portion 140 of the articulating tip 40 abuts the endometrial lining of the uterus. Next, when the trigger mechanism 60 is actuated by pulling the trigger 65 a distance inward toward the handle 10, the articulating tip 40 will curl in the planar direction as set by the rotating knob 90 and at an angular distance θ proportionate to the degree the trigger 65 is pulled. The articulating tip 40 will create a small abrasion on the lining of the uterus. After the abrasion is made, when the handle 10 is slowly released, the spring-loaded trigger mechanism 60 operates to bring the articulating tip 40 back to its resting state, which is a state of longitudinal alignment with the rigid portion 100 of the arm 20. At this stage, the arm 20 can be safely and easily manually removed from the uterine cavity by the physician.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical." Numerous modifications and adaptations will be readily apparent to those skilled in this art without departing from the spirit and scope of the present invention.

What is claimed is:

1. A method for improving implantation of a fertilized egg during pregnancy, said method comprising the steps of:
   a. providing a medical device for creating a small, precise abrasion on an endometrium layer of a patient's uterus prior to artificial insemination, said device comprising:
      i. a handle;
      ii. an arm comprising a rigid portion and an articulating tip extending along a longitudinal axis of the arm, wherein the rigid portion and the articulating tip each have a proximal end and a distal end, wherein the distal end of the rigid portion is connected to the proximal end of the articulating tip;
      iii. a connecting member comprising a trigger mechanism; and
      iv. a sleeve with a rounded cap portion disposed at a distal end of the sleeve such that the sleeve and cap portion form a contiguous body, wherein the cap portion is configured such that the cap portion is unable to open, wherein the sleeve and cap portion are adapted to fully enclose the arm, wherein said cap portion comprises a uniform exterior curved surface that is smooth and free of any protrusions and indentations,
      v. wherein the handle is connected to the proximal end of the rigid portion of the arm by the connecting member,
      vi. wherein the trigger mechanism is operable to curl the articulating tip,
   b. introducing the medical device into the patient's uterine cavity prior to ovulation;
   c. contacting the distal end of the articulating tip with the endometrium layer of the uterus;
   d. actuating the trigger mechanism to operably curl the articulating tip;

e. making a small abrasion on the endometrium layer of the uterus with the articulating tip;
f. releasing the trigger mechanism allowing the articulating tip to return to its original position; and
g. removing the medical device from the patient.

2. The method of claim 1 wherein the medical device further comprises a rotatable knob, said knob is operable to adjust the curling direction of the articulating tip.

3. The method of claim 1 wherein the step of actuating the trigger mechanism to operably curl the articulating tip comprises curling the articulating tip up to 90° from the longitudinal axis of the arm.

* * * * *